US00PP08094P

United States Patent [19]

Zaiger et al.

[11] Patent Number: Plant 8,094

[45] Date of Patent: Jan. 12, 1993

[54] NECTARINE TREE "ARTIC QUEEN"

[76] Inventors: Chris F. Zaiger, 537 Rosemore Ave.; Leith M. Gardner, 1207 Grimes Ave.; Gary N. Zaiger, 1907 Elm Ave.; Grant G. Zaiger, 4005 California Ave., all of Modesto, Calif. 95351

[21] Appl. No.: 769,111

[22] Filed: Sep. 30, 1991

[51] Int. Cl.[5] ..... A01H 5/00

[52] U.S. Cl. ..... Plt./41.1

[58] Field of Search ..... Plt./41.1

*Primary Examiner*—James R. Feyrer

[57] ABSTRACT

A new and distinct variety relates to a nectarine tree which has the following unique combination of desirable features:

1. Production of white flesh fruit with excellent flavor and eating quality.
2. Heavy and regular bearing of fruit.
3. Firm flesh texture with good handling and shipping quality.
4. Vigorous upright growth.
5. Production of fruit with an attractive red skin color.
6. Relatively uniform ripening of fruit.

ORIGIN OF THE VARIETY

The present new variety of nectarine tree waas originated by us in our experimental orchard located near Modesto, Calif., as a first generation cross between two selected nectarine seedlings with the field identification numbers 32EB252 and 35GC20. The maternal parent 32EB252 originated from a second generation cross between two selected seedlings. One with the parentage of Sun Grand Nectarine (U.S. Plant Pat. No. 974) crossed with Merril Gem Peach (U.S. Plant Pat. No. 868) and the other seedling was selected from a second generation cross between a late maturing nectarine of unknown parentage

1 Drawing Sheet

ASEXUAL REPRODUCTION OF THE VARIETY

The present new variety of nectarine tree was asexually propagated by budding, as performed by us in our experimental orchard located near Modesto, Calif., and shows that all characteristics come true to the original tree and are established and transmitted through succeeding propagations.

SUMMARY OF THE VARIETY

The new and distinct variety of nectarine tree which is of large size, upright vigorous growth, medium dense and a productive and regular bearer of large, white flesh, freestone fruit with excellent flavor and eating quality. The fruit is further characterized by having an attractive red skin color, firm flesh texture with good handling and shipping qualities and the ability to ship to long distance markets.

PHOTOGRAPHS OF THE VARIETY

The accompanying color photographs show typical specimens of the fruit and foliage of the present nectarine variety, with the upper and lower surface of the leaves being shown, the exterior and a cross sectional view of the fruit being divided in the suture plan to reveal flesh coloration with a stone remaining in place. The photographs were taken shortly after being picked at maturity (firm ripe) and the colors are as nearly true as is reasonably possible in a color representation of this type.

DESCRIPTION OF THE VARIETY

The following is a detailed botanical description of our new variety of nectarine tree, its flowers, foliage, and fruit with color definitions (except those in common terms) referenced to Reinhold Color Atlas by A. Kornerup and J. H. Wanscher.

Tree:
- *Size.*—Large.
- *Vigor.*—Vigorous.
- *Form.*—Upright.
- *Density.*—Medium dense.
- *Productivity.*—Productive.
- *Bearing.*—Regular.

Trunk:
- *Size.*—Medium stocky.
- *Surface.*—Medium shaggy.
- *Color.*—Brown to grayish brown (5-D-5) to (5-E-4).

Branches:
- *Size.*—Medium.
- *Surface.*—Smooth to medium rough.
- *Lenticels.*—Medium number. Small in size.
- *Color.*—New Growth — light brown (5-E-7). Old Growth — brown (5-E-5).

Leaves:
- *Size.*—Large. Average length — 6". Average width — 1½".
- *Surface.*—Smooth to slightly rugose.
- *Petiole.*—Medium length. Medium width.
- *Form.*—Lanceolate. Acutely pointed.
- *Margin.*—Crenate.
- *Glands.*—Reniform. Number varies from 2 to 6. Average number 4. Medium size. Positioned on base of leaf blade and upper portion of petiole.
- *Color.*—Upper surface — green (27-E-7) (27-F-7). Lower surface — dull green (27-D-5) to (27-E-5).

Flower buds:
- *Size.*—Medium to large.
- *Form.*—Plump.
- *Length.*—Medium.

Flowers:

*Blooming period.*—Mar. 5, 1990 to Mar. 11, 1990. Varies slightly with climatic conditions.

*Size.*—Large — showy.

*Pollen.*—Present — self fertile.

*Color.*—Pink.

Fruit:

*Maturity when described.*—Firm ripe.

*Date of first picking.*—Jul. 24, 1990.

*Date of last picking.*—Jul. 30, 1990.

*Size.*—Large. Average diameter axially — $2\frac{7}{8}$. Average transversely in suture plane — $2\frac{5}{8}$.

*Form.*—Nearly globose, only slightly elongated.

*Suture.*—Shallow, nearly smooth, extends from base to apex.

*Ventral surface.*—Usually rounded, very slightly lipped.

*Cavity.*—Rounded to slightly elongated in suture plane. Average depth — $2\frac{1}{2}$. Average breadth — $\frac{3}{4}$.

*Base.*—Retuse.

*Apex.*—Varies from rounded to very slight pistil point.

Skin:

*Thickness.*—Medium.

*Texture.*—Tough, tenacious to the flesh.

*Tendency to crack.*—None.

*Down.*—Wanting.

*Color.*—White to yellowish white (4-A-1) to (4-A-2). Nearly overspread with orange red to lobster red (8-B-8) to (9-B-8).

Flesh:

*Ripens.*—Evenly.

*Texture.*—Firm.

*Juice.*—Moderate.

*Fibers.*—Few, tender.

*Flavor.*—Excellent, mild, sub-acid, sweet.

*Aroma.*—Moderate.

*Eating quality.*—Excellent.

*Amygdalin.*—Undetected.

*Color.*—White to pinkish white (7-A-1) to (7-A-2). Pit cavity — red to brownish red (9-C-8) to (10-C-8) with bleeding of red from pit cavity into flesh, heavier near apex. Slight light gray callus from stone in pit cavity.

Stone:

*Type.*—Freestone.

*Size.*—Medium. Average length — $1\frac{1}{8}''$. Average width — $\frac{3}{4}$. Average thickness — $\frac{1}{2}''$.

*Form.*—Ovoid.

*Base.*—Usually rounded, varies from straight to rounded.

*Apex.*—Acuminate.

*Sides.*—Varies from equal to unequal.

*Surface.*—Furrowed toward apex, pitted toward base. Pits vary from elongated to round.

*Ridges.*—Usually rounded toward apex.

*Tendency to split.*—None.

*Color.*—Brown to dark brown (7-E-6) to (7-E-8).

Use: Dessert. Markets, local and long distance.

Keeping quality: Good.

Shipping quality: Good.

The present nectarine tree, its flowers and fruit herein described may vary in slight detail due to climatic, soil conditions and cultural practices under which the variety may be grown; the present description is that of the variety grown under the ecological conditions prevailing near Modesto, Calif.

We claim:

1. A new and distinct variety of nectarine tree, substantially as illustrated and described, characterized by its large size, vigorous upright growth and a productive and regular bearer of large, white flesh, freestone fruit with excellent flavor and eating quality; the fruit is further characterized by being relatively uniform in ripening, having an attractive red skin color, with firm flesh texture and good handling and shipping qualities.

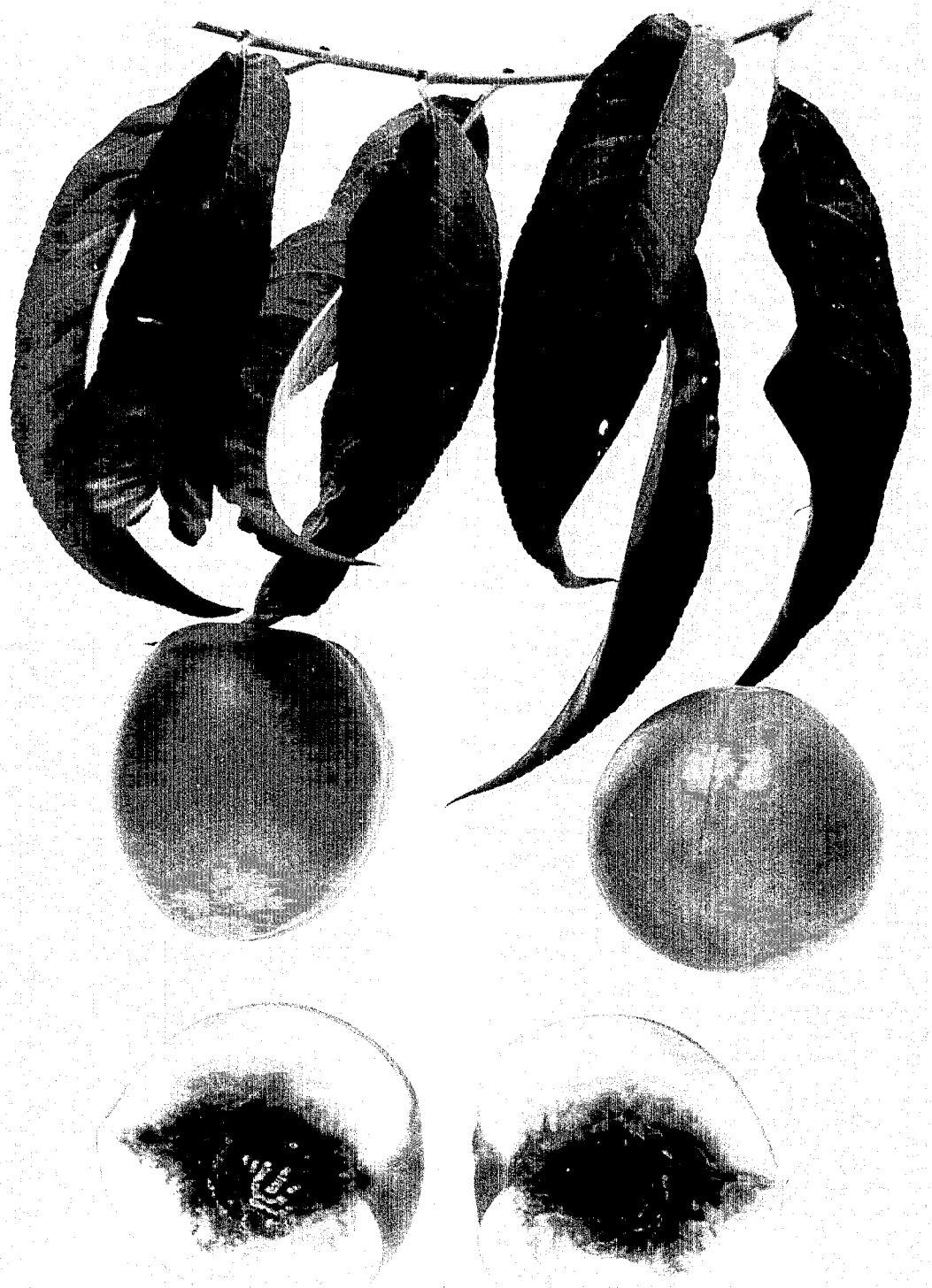

* * * * *